(12) United States Patent
Prince et al.

(10) Patent No.: US 11,998,359 B2
(45) Date of Patent: Jun. 4, 2024

(54) AUTOMATED ALLERGY OFFICE

(71) Applicants: Ty L. Prince, Knoxville, TN (US);
Herman J. Novak, Maryville, TN (US)

(72) Inventors: Ty L. Prince, Knoxville, TN (US);
Herman J. Novak, Maryville, TN (US)

( * ) Notice: Subject to any disclaimer, the term of this patent is extended or adjusted under 35 U.S.C. 154(b) by 0 days.

(21) Appl. No.: 18/185,827

(22) Filed: Mar. 17, 2023

(65) Prior Publication Data

US 2023/0218234 A1    Jul. 13, 2023

Related U.S. Application Data (63) Continuation-in-part of application No. 18/078,856, filed on Dec. 9, 2022, which is a continuation-in-part of application No. 17/992,125, filed on Nov. 22, 2022, now Pat. No. 11,696,722, which is a continuation-in-part of application No. 17/468,132, filed on Sep. 7, 2021, now Pat. No. 11,369,782, and a continuation-in-part of application No. 17/402,413, filed on Aug. 13, 2021, now Pat. No. 11,517,249.

(60) Provisional application No. 63/362,623, filed on Apr. 7, 2022, provisional application No. 63/289,350, filed on Dec. 14, 2021.

(51) Int. Cl.
*A61B 5/00* (2006.01)
*G16H 70/20* (2018.01)

(52) U.S. Cl.
CPC ............... *A61B 5/70* (2013.01); *A61B 5/411* (2013.01); *A61B 5/7264* (2013.01); *A61B 5/7445* (2013.01); *A61B 5/749* (2013.01); *G16H 70/20* (2018.01)

(58) Field of Classification Search
CPC ......... A61B 5/70; A61B 5/411; A61B 5/7264; A61B 5/7445; A61B 5/749; G16H 70/20
USPC ....................................................... 600/556
See application file for complete search history.

(56) References Cited

U.S. PATENT DOCUMENTS

| 4,819,657 A | 4/1989 | Kraft et al. |
|---|---|---|
| 10,197,803 B2 | 2/2019 | Badiali et al. |
| 2015/0025412 A1 | 1/2015 | Gillman et al. |
| 2016/0026765 A1 | 1/2016 | Daines et al. |
| 2017/0177802 A1 | 6/2017 | Smith |
| 2019/0065464 A1 | 2/2019 | Finley et al. |
| 2020/0202245 A1 | 6/2020 | Lesnik et al. |
| 2020/0211420 A1 | 7/2020 | Buras et al. |

FOREIGN PATENT DOCUMENTS

| WO | 2017044691 | 3/2017 |
|---|---|---|

*Primary Examiner* — Alex M Valvis
*Assistant Examiner* — Chanel J Jhin
(74) *Attorney, Agent, or Firm* — Rick Barnes (57) ABSTRACT

The automated allergy office system and method takes a medical professional through an allergy testing process and a follow-on immunology injection process step-by-step using LED computer screen tables, computer tablets, smart phones, an internal office computer system accessing Patient medical records, and an augmenter reality headset. The augmented reality headset technology and artificial intelligence are layered onto an improved manual system to minimize false positives and negatives, to improve the patient experience patient, resulting in cost savings for the doctor and patient and enabling portions of the allergy testing to be performed remotely from the office of the allergist, either by the patient or by a trained medical technician.

7 Claims, 6 Drawing Sheets

AUTOMATED ALLERGY OFFICE

PRIORITY

This application is a continuation-in-part of prior pending U.S. patent application Ser. No. 18/078,856 filed 2022 Dec. 9, which claims priority on:
U.S. provisional patent application Ser. No. 63/289,350 filed 2021 Dec. 14, U.S. provisional patent application Ser. No. 17/402,413 filed 2021 Aug. 13, U.S. provisional patent application Ser. No. 17/468,132 filed 2021 Sep. 7, U.S. provisional patent application Ser. No. 17/992,125 filed 2022 Nov. 22;
and also claims priority on prior U.S. provisional patent application Ser. No. 63/362,623 filed 2022 Apr. 7.

RELATED APPLICATIONS

This application is related to U.S. provisional patent application Ser. No. 62/727,136, entitled "Safety Syringe Assembly" (Prince), filed on Sep. 5, 2018; U.S. provisional patent application Ser. No. 63/106,793, Entitled "Single and Multiple Allergen Skin Testing System" (Prince) filed on Oct. 28, 2020; U.S. patent application Ser. No. 16/983,268 entitled "Processes for Utilizing Safety Syringe Assemblies" (Prince) filed on Aug. 3, 2020, which is related to and a continuation-in-part of U.S. patent Ser. No. 10/765,814 entitled "Safety Syringe Assembly" (Prince) filed on Sep. 8, 2020.

FIELD

The present invention relates to allergy testing, and more particularly to computer-based assessment of allergy skin results in a minimally invasive manner. The present invention also uses artificial intelligence and augmented reality to guide medical professionals to perform their testing and injection duties with significantly fewer mistakes.

INTRODUCTION

To avoid an allergic reaction, people need to know what a patient is allergic to. Skin testing is one way a doctor can check on what causes your symptoms. These tests use extracts (a concentrated liquid form) of common allergens such as pollen, mold, dust mites, animal dander, and foods. Once those get under the skin of the patient, they could trigger a reaction called a wheal and flare. An allergy may trigger an itch, like a mosquito bite. That reaction is how the doctor can tell a patient's allergies. When a patient has an allergy, the patient's immune system will make antibodies and set off chemicals to fight off the trigger.

The prior art describes allergy testing systems that are burdensome and add complicated steps to the process of patient analysis and treatment.

United States patent publication 20170177802 depicts an allergy service management portal including systems, programs, and methods for an allergy management system (AMS). In general, the AMS provides a system through which a user may manage allergy-related care for one or more patients. In one embodiment, the AMS includes an application executed on a computing device, such as a tablet or other type of mobile computing device, which provides an interface for the user to manage various information and/or algorithms to aid the practitioner in providing the allergy care. Further still, the AMS may receive measurement information of a skin wheal test of a patient from a scanner component of a computing device and utilize that measurement information to aid the practitioner in the patient care.

United States patent publication 20160026765 depicts an immunotherapy system and method. One aspect of the system and method involves the system generating a patient specific immunotherapy treatment recommendation that includes a network interface configured to receive a first input, second input and third input. A first input includes information having characteristics indicative of a patient's medical history, a second input includes information having characteristics indicative of one or more science factors, and a third input includes information having characteristics indicative of a patient's immune response to one or more antigens of a test.

United States patent publication 20150025412 depicts an allergy skin testing kit. The kit includes a template having puncture site indicators and a computer-readable storage medium storing allergy test information that associates the puncture site indicators of the template with template locations or test substance indicators. A method of performing an allergy skin test includes providing a template having puncture site indicators. Allergy test information that associates the puncture site indicators of the template with template locations or test substances identifiers is obtained. Image data corresponding to a test area on the skin of a test subject obtained and image regions corresponding to the puncture site indicators of the template are identified. Test results corresponding to the image regions are determined based, at least in part, on the allergy test information.

U.S. Pat. No. 4,819,657 depicts an automatic allergy testing system. The system includes an electrode capable of testing up to eight different allergies and an associated electronic unit. The electrode includes apparatus to deliver an allergen to the patient without puncturing the patient's skin. The electrode also includes a temperature sensor for sensing the skin temperature in the area surrounding the delivery of the allergen. Electronic apparatus is provided for processing the sensed temperature and storing data related thereto for subsequent print out to an output device. The allergy testing system is controlled so that periodic temperature readings are made at thirty second intervals over approximately a 15-minute testing span. The data can be printed out in a graphic format to allow the physician to easily and quickly make more accurate diagnosis.

PCT publication 2017044691 describes systems and methods of providing allergy-related medical services using inventory control methods. Computer-mediated verification of antigens are used in allergy testing and treatment and visual matching of materials to virtual representations of the materials. The systems and methods describe allergy test kit preparation, allergy test scoring, penicillin allergy testing, compounding patient immunotherapy vial sets, recording immunotherapy progress, and other administrative processes.

Recent technological breakthroughs in the areas of artificial intelligence, augmented reality displays, identification tagging and labeling, home health care, skin testing and others require that some testing practices be re-examined to confirm that best practices are being effectively used.

What is needed is an allergy testing system and method that uses the power of electronics, software, databases, artificial intelligence learning, augmented reality display technology, electronic displays, and computer systems, overlaid on top of improved manual systems, to minimize false positives or negatives, to improve the patient experience, and to reduce the cost of the current manual process and speed the billing process.

Therefore, there is a need for an allergy testing system and method that is minimally invasive and which causes minimal discomfort to the patient, which can be initiated and periodically updated either remotely or in the allergist's office, which provides improved accuracy, reduces false positives and false negatives, which is cost-effective, and which is easy to use and manufacture.

What is also needed is an allergy testing system and method that minimizes the opportunity for errors in the complicated system of testing, analyzing, and treating a patient with allergies.

SUMMARY

The automated allergy office of the present disclosure addresses the needs outlined above.

A first embodiment of the automated allergy office system and method of the present disclosure takes a medical professional through an allergy testing process and a follow-on immunology injection process step-by-step using LED computer screen tables, computer tablets, smart phones, an internal office computer system accessing the Patient's medical records, and an augmented reality headset. The augmented reality headset technology and artificial intelligence are layered onto an improved manual system to minimize false positives and negatives, to improve the patient experience, resulting in cost savings for the doctor and patient and enabling portions of the allergy testing to be performed remotely from the office of the allergist, either by the patient or by a trained medical technician. The testing vials, the patient specific immunology vials, and the skin test target tags and the patient, in some embodiments, each deploy either radio frequency ID tags, Bluetooth low energy tags, or near field communication tags.

A second embodiment of the automated allergy office system of the present disclosure comprises back or arm target stickers used by artificial intelligence and augmented reality headset as sites such that the system determines target locations of where to perform scratch or injection points, wherein moles, skin tags, pre-existing rash or tattoo, that may yield a false positive or negative display a message for a medical technician to move the back or arm target sticker to a scratch or injection point away from the mole, skin tag, pre-existing rash or tattoo. If the patient has the mole or skin tag as identified by the artificial intelligence or the augmented reality headset, a second test site is identified. The second test site reduces the likelihood of false positives and negatives. The automated allergy office system of the present disclosure may be initiated either in the office of the allergist or remotely. The automated allergy office system of the present disclosure may be periodically updated either in the office of the allergist or remotely.

A third embodiment of the automated allergy office system of the present disclosure including an augmented reality headset that projects target allergen injection points on the image of the back or arm of the patient relative to the target location wherein if the augmented reality headset detect a mole or skin tag at the target location is moved to avoid the mole or skin tag. The augmented reality headset combined with voice recognition technology interprets spoken commands of a wearer of the augmented reality headset. The augmented reality headset reads and records the wheal color, and diameter, and the diameter of the flare. In another embodiment, the augmented reality headset also reads and records an infrared signature of a wheal reaction site and flare reaction site. A second embodiment of the automated allergy office system of the present disclosure also includes means for retesting negative test results. The retesting of the negative test results is performed using prefilled vials and syringes, wherein the augmented reality headset monitors the content of each vial, each vial location in a testing tray, temperature of the vials to ensure they do not get too hot or too cold and the location of each skin test. In addition, the augmented reality headset monitors injection sites and the location of the used skin testers and the location of used vials.

A fourth embodiment of the automated allergy office system of the present disclosure comprises artificial intelligence learning of the correct interpretation of wheal, flare, color, and infrared temperature measurement, including grading, the artificial intelligence through an augmented reality headset, recording each test site to ensure that the interpretation of the injection site is analyzed correctly. The augmented reality headset captures an image of a test site immediately after an allergen is administered. The augmented reality headset also captures an image of a test site at about a 20-minute interval after the tests are completed. The automated allergy office system of the present disclosure further comprise means for updating artificial intelligence models with current values. Such updated artificial intelligence models are designed for achieving optimal values while safeguarding patient identity in an artificial intelligence library.

The automated allergy office of the present disclosure comprises preloaded allergy testing vials, preloaded allergy multi testing trays and an automated process for filling patient immunology vials. It also uses the latest technology for patient data entry (phone or tablet app), identifying a patient (a biometric—such as face, finger, voice, or a combination of thereof), processing the patient when the patient visits the office, the ability for home allergy testing, an augmented reality system to help to eliminate mistakes in the testing process, inventory, the data recording process, the analysis process, the immunology process and the billing process. This automated allergy office of the present disclosure eliminates the need to place marks on a patient's back or arm, to identify allergen test sites, it also eliminates the need to put marks on a patients arm or back for subsequent intradermal injection tests performed only if individual tests are negative on percutaneous tests. Since the system has a built-in timer, the nurse will be notified when a user reaches the 20-minute time has elapsed when the scratches or injections were initially applied. This time out period will instruct the nurse to return to the exam room where the positive, negative analysis will be completed. The system is designed to step the nurse or doctor through the allergy testing process and the follow-on immunology injection process with the use of LED computer screen tables, computer tablets, smart phones, an internal office computer system (patient records and billing) and augmenter reality headset.

The automated allergy office system and method of the present disclosure reads wheal size change, flare size change, wheal, and flare color as well as wheal and flare temperature. Using the traditional method of reading wheal size change and flare size and color, it is difficult to analyze these changes on a person with dark skin or tattoos. By adding wheal and flare color analysis and wheal and flare temperature change, the interpretation of a positive or negative reaction on a patient with a darker skin complexion or with tattoos will be greatly improved.

Still other aspects of the processes for utilizing the automated allergy office of the present disclosure will become apparent to those skilled in this art from the following description wherein there is shown and described various embodiments, simply by the way of illustration of the modes contemplated for carrying out the present disclosure. As will be realized, the present disclosure is capable of different embodiments, and its several details are capable of modification in various, obvious aspects all without departing from the disclosure. Accordingly, the drawings and descriptions will be regarded as illustrative in nature and not as restrictive.

BRIEF DESCRIPTION OF THE DRAWINGS

Further advantages of the embodiments are apparent by reference to the detailed description when considered in conjunction with the figures, which are not to scale so as to show the details more clearly, wherein like reference numbers indicate like elements throughout the several views, and wherein.

DESCRIPTION

With reference now to the drawings, there are depicted all of the claimed elements of the various embodiments, although all claimed embodiments might not be depicted in a single drawing. Thus, it is appreciated that not all embodiments include all of the elements as depicted, and that some embodiments include different combinations of the depicted elements. It is further appreciated that the various elements can all have many different configurations, and are not limited to just the configuration of a given element as depicted. As indicated above, the elements of the drawings as depicted are not to scale, even with respect one to another, and relative size or thickness of one element cannot be determined by the aspect ratios of that element or with reference to any dimension of another element.

Figure 1:
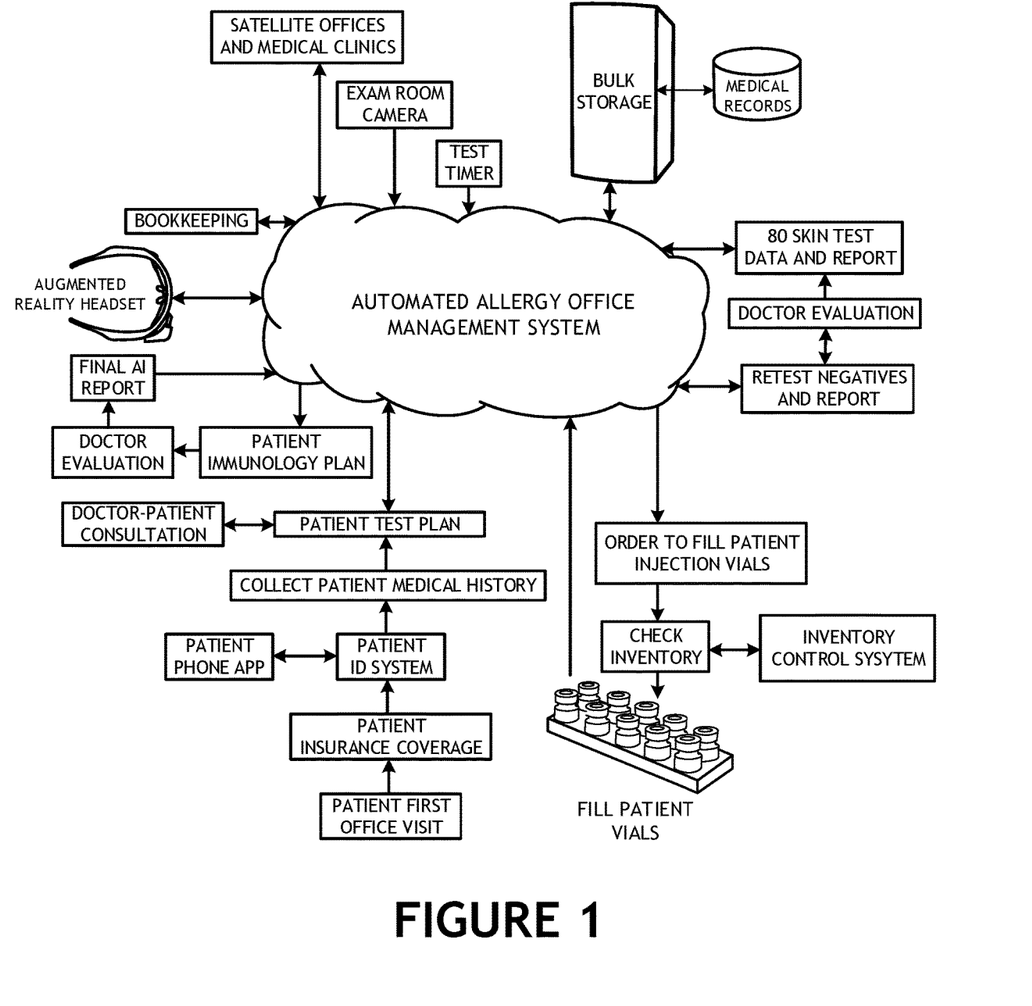
FIG. 1 depicts a first embodiment of the automated allergy office of the present disclosure.
Figure 2A:
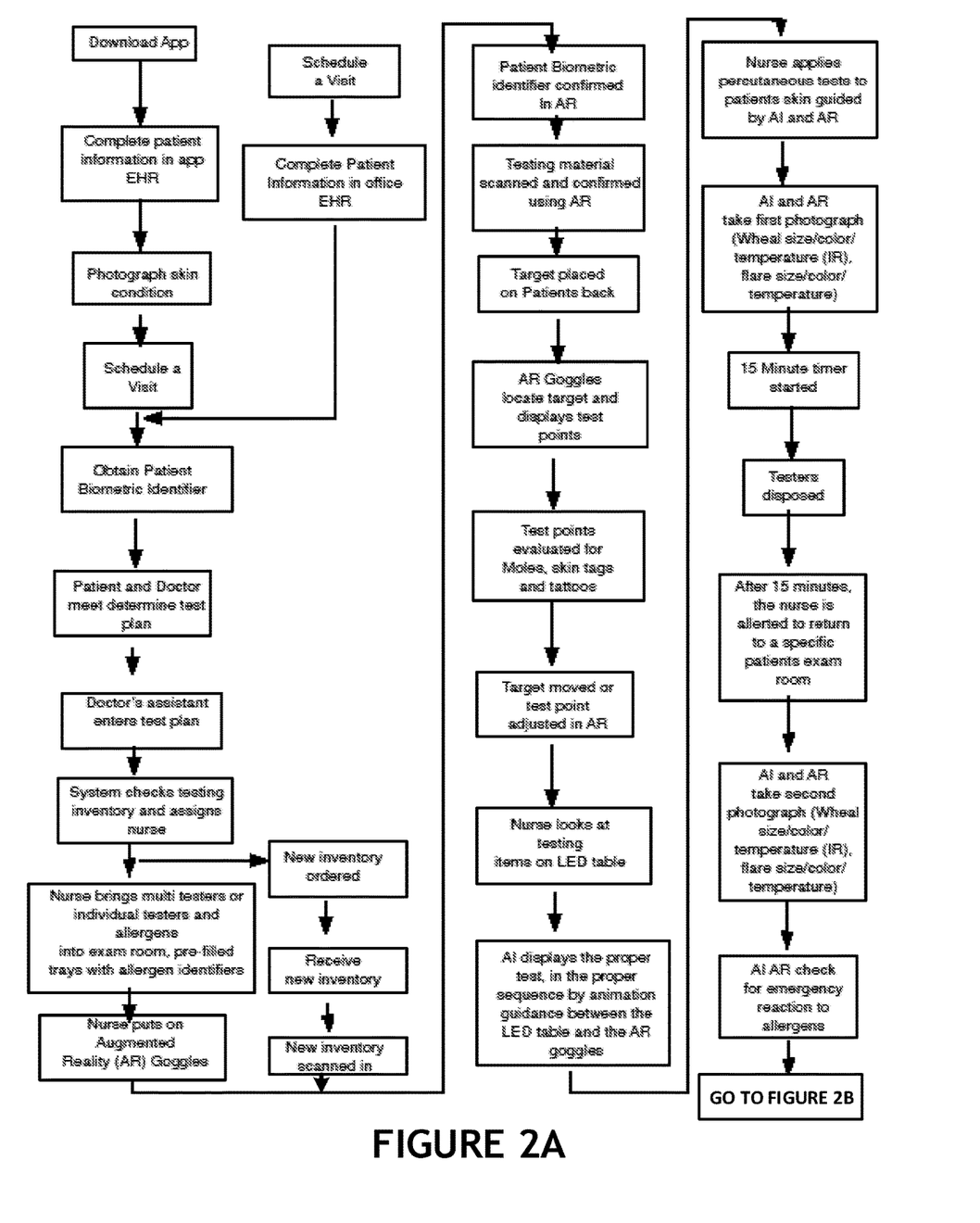
FIGS. 2A, 2B, 2C, 2D, and 2E depict the operations performed in the simplified schematic layout of the automated allergy office of the present disclosure.
Figure 2B:
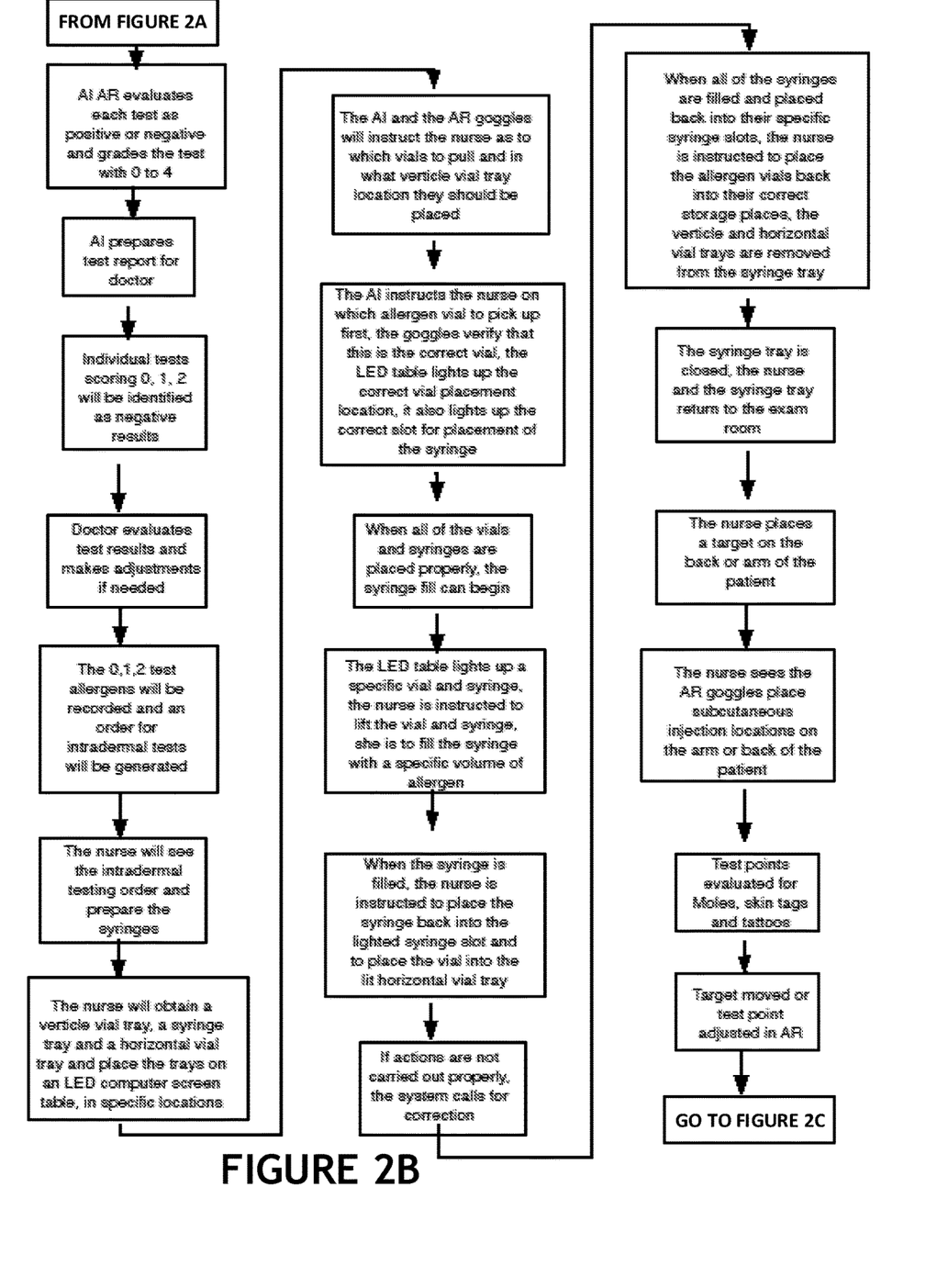
Figure 2C:
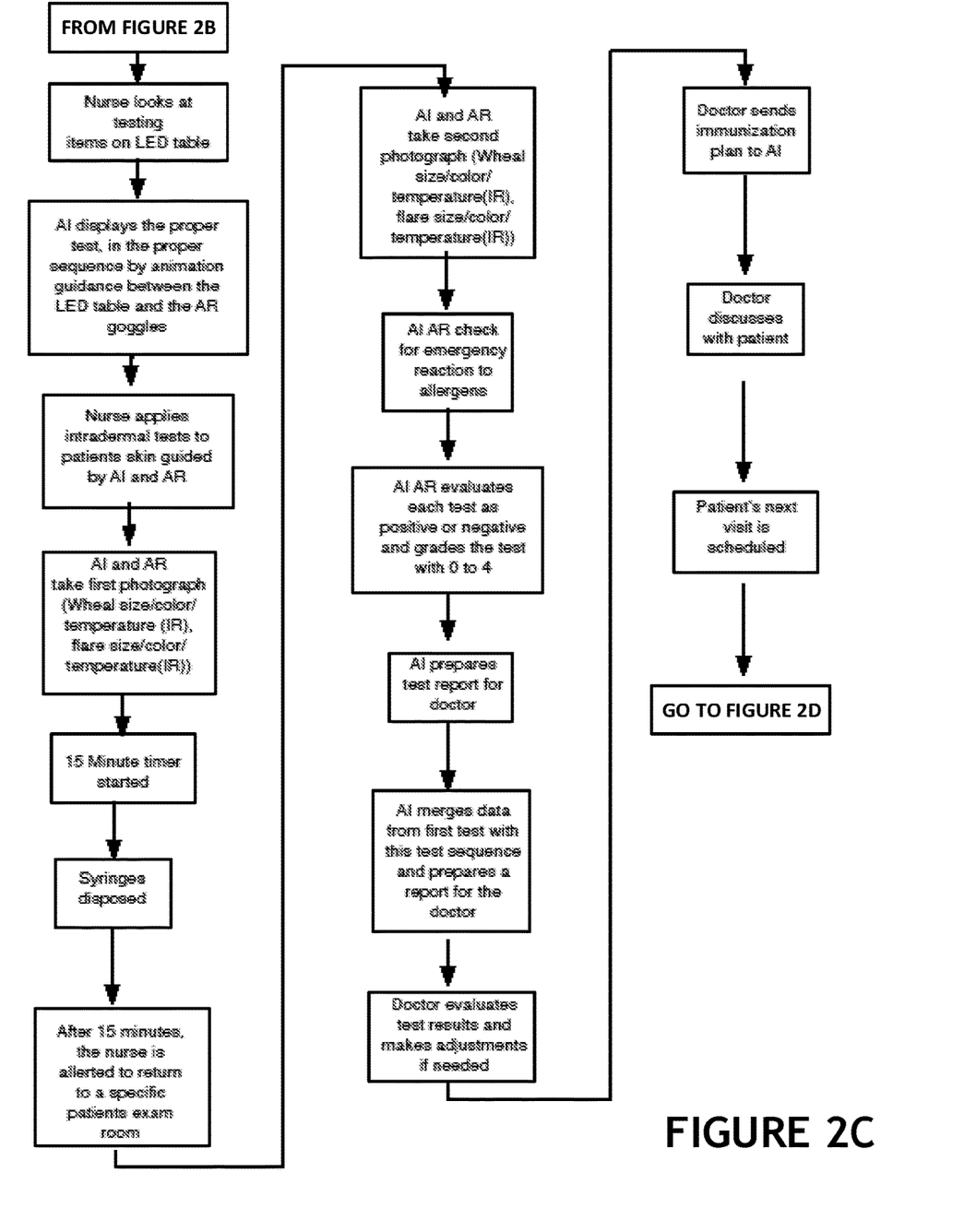
Figure 2D:
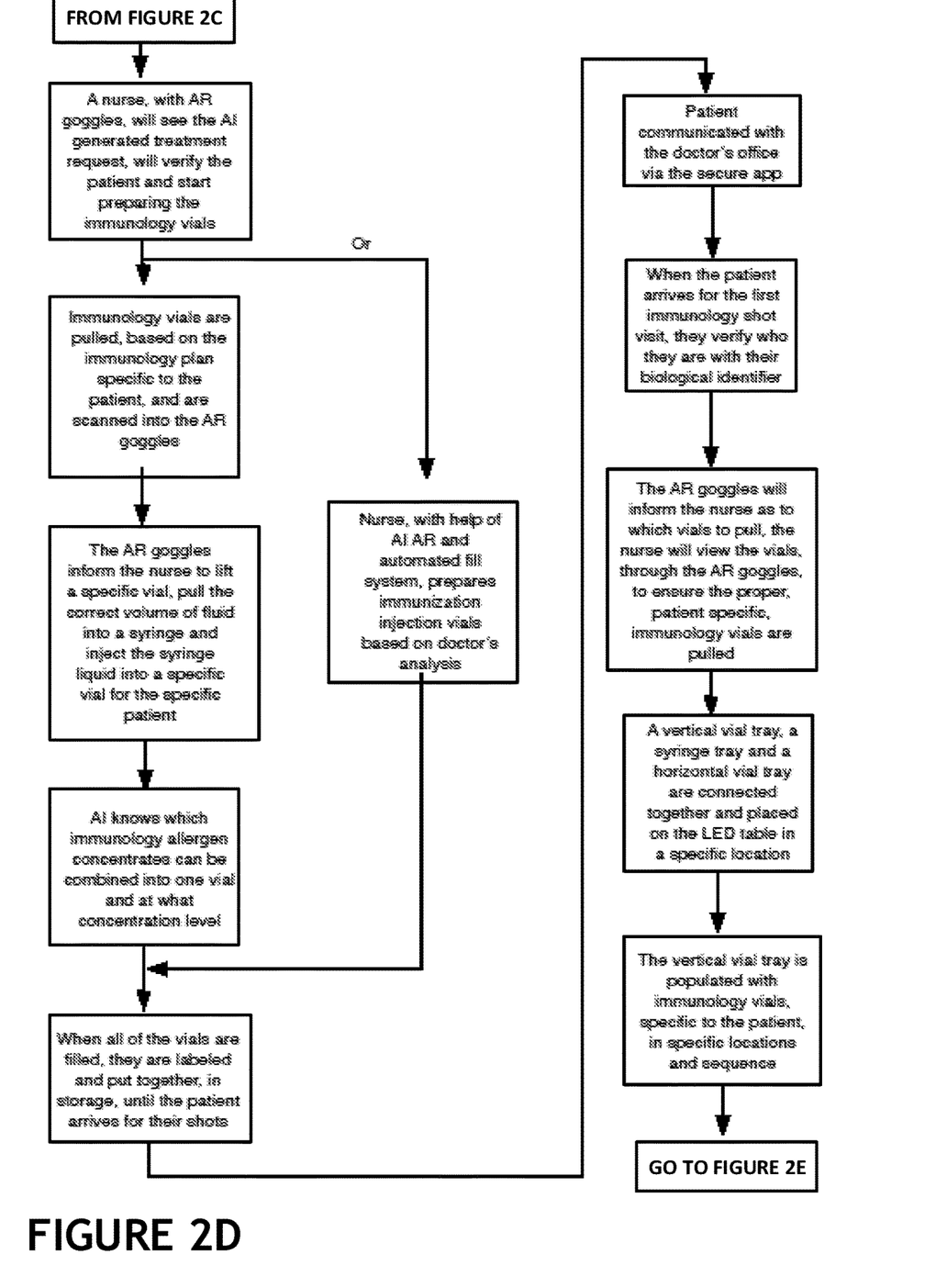
Figure 2E:
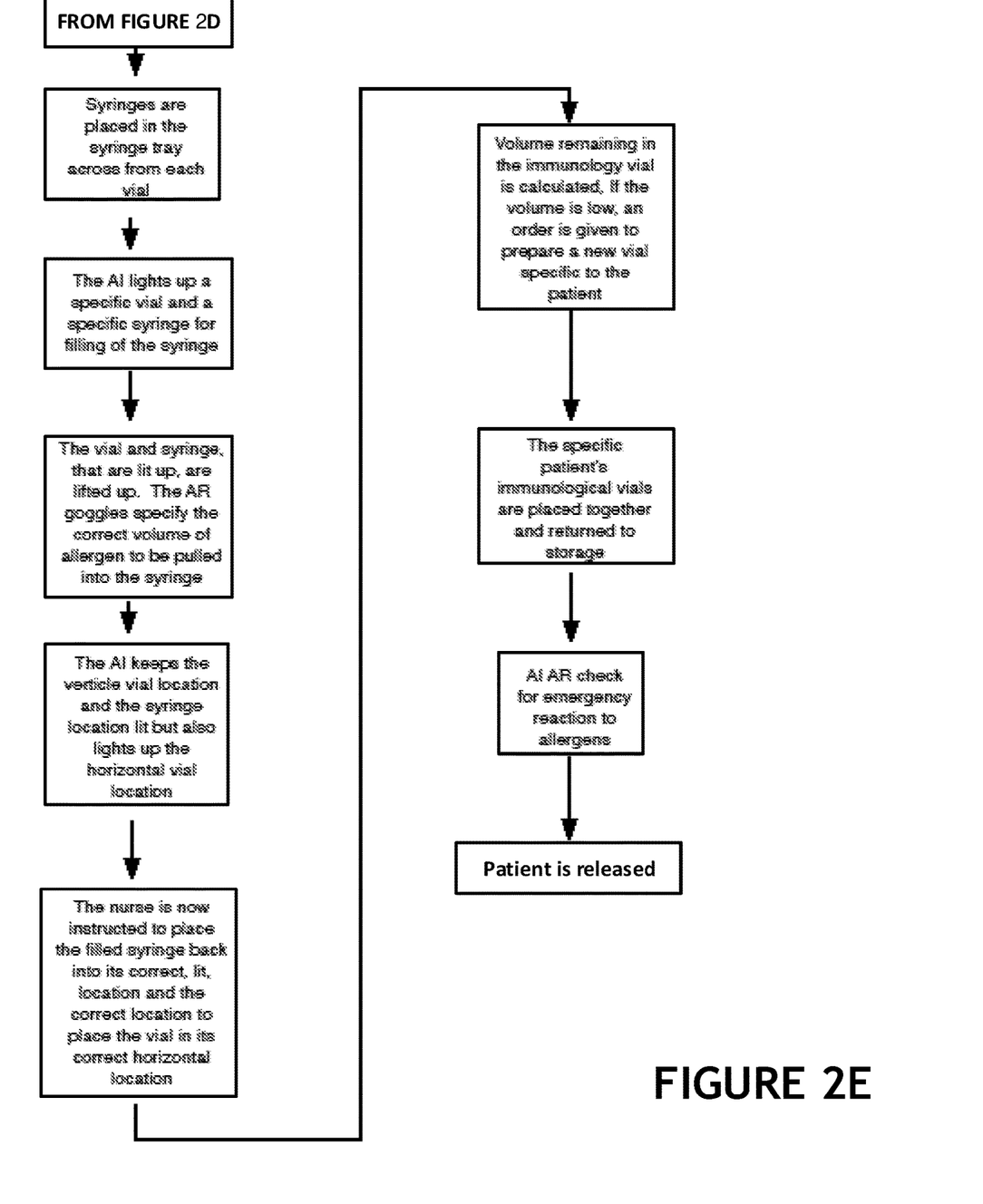

Referring now to the drawings, FIG. 1 depicts a first embodiment of the automated allergy office of the present disclosure.

A phone or tablet app for the patient is used to input personal and medical information prior to or during the initial office visit. This includes symptoms, photographs of skin rashes with the color of rash and temperature of any rash being recorded as part of the patient's record along with any other indications that are unusual or new.

The patient schedules a consultation with the allergist by phone or tablet app. The consultation can either be a visit to the allergist's office, a visit to some other medical facility, or a phone consultation. If the initial visit between the patient and doctor is done remotely, for example, if the patient is home-bound, the skin tests can be performed by a nurse or medical technician from the doctor's office visiting the patient. Similarly, if the patient is home-bound and follow-up testing is required, the tests can be performed by a nurse or medical technician from the doctor's office visiting the patient. Satellite offices and medical clinics can also be incorporated into the system.

The patient's medical history and insurance information is obtained during the initial doctor-patient contact. The medical history may also be submitted by written forms, by phone, or a tablet app or entered by the patient on a website. This includes symptoms, photographs of skin rashes with the color of rash and temperature of any rash being recorded as part of the patient's record along with any other indications that are unusual or new.

Also, one or more of the patient's biometric identifiers are obtained (e.g.—face, finger, voice). Bimodal identification is used in one embodiment.

In addition, FIGS. 2A, 2B, 2C, 2D, and 2E depict the operations performed in a simplified schematic layout of the automated allergy office of the present disclosure.

The automated allergy office of the present disclosure includes clear, single tester, multi tester and vial trays. The testing vials, patient specific immunology vials, and skin test target tags, will use the latest ID tag technology.

RFID tags which have an antenna and receives power, via an RF field, generated by the RFID tag reader are used. Bluetooth low energy tags are also used. Near field communication tags are also used. Wiliot provides near field communication tags for the electronic tracking of medication, flexible electronic connectivity, and battery-free sensor tags. These tags enable the electronic tracking and monitoring of medication dispensing and intake. The kit is a multi-vial box covered with a cardboard layer of continuously numbered, perforated areas corresponding to the individual compartments. When the user opens a perforation at the starter tab the removal of the vial will be tracked by means of integrated, printed electronics.

The Bluetooth low energy tags and the near field communication tags include electronics and memory imbedded in a tag that needs no external power source, it obtains its needed power by harvesting energy from the RF signals that are present in homes and offices, such as Wi-Fi router signals.

A near field communication tag supplied by Wiliot that is glued to a simple antenna printed on plastic or paper can authenticate the proximity of a product by transmitting an encrypted serial number along with weight and temperature data from a device the size of a postage stamp Eliminating most of the components associated with traditional Bluetooth, these tags lower sale and maintenance costs to previously unachievable levels.

These tags communicate with the office automation system through secure Wi-Fi or even through the augmented reality headset.

This embodiment of the automated allergy office includes a table-top LED display.

The augmented reality headset, in some embodiments, includes voice recognition that understands the voice of the nurse, will read the color and size of the wheal and flare, and will read the infrared signature of the wheal and flare reaction site.

The driver for the augmented reality headset may be a computer, a tablet, or a secure Wi-Fi network.

The prefilled single tester tray, in some embodiments, uses a barcode, a QR-type code or some other identifier. The prefilled multi tester tray uses a barcode, a QR-type code, or some other identifier. Prefilled allergen vials use a barcode, a QR-type code, or some other identifier.

The trays are scanned with the augmented reality headset. Even though the trays are preloaded, the augmented reality headset serves to record what was given to the patient.

Back or arm target stickers are used by the artificial intelligence and an augmented reality headset as a location point such that the system knows were to display the scratch or injection points (moles, skin tags, pre-existing rash or tattoos, that could cause the system to locate a scratch point or an injection point that may give a false positive or negative, will display a message for the nurse to move the target sticker or will automatically move the injection point away from the mole, skin tag, pre-existing rash or tattoo).

The augmented reality headset captures the image of the test sites immediately after each test is completed as well as 20 minutes after the tests are completed.

The system guides the nurse through the testing and injection process. However, if for some reason the nurse exits the system or allows the system to go into a sleep mode, such as if there is something that interrupts the process and causes her to leave, when she returns, the system identifies the point in the process at which she stopped, and prompts her to continue from that point. Thus, she does not need to be concerned about either duplicating or skipping any of the procedures.

After twenty minutes, the nurse returns to the exam room so that the system can perform the final data collection and analysis. It is important to return to the exam room after the 20 minutes because some wheal and flare reactions can dissipate quickly after 25-30 minutes. An accurate analysis timed after 20 minutes will help to minimize the number of false positives or negatives.

If the artificial intelligence sees a reaction that may harm the patient, the system signals the nurse or doctor to see the patient immediately. The testing process is timed.

The automatic filling system for immunotherapy vials is identified and locked by the biometric identifier of the patient.

A first embodiment of the automated allergy office system and method of the present disclosure takes a medical professional through an allergy testing process and a follow-on immunology injection process step-by-step using LED computer screen tables, computer tablets, smart phones, an internal office computer system accessing the patient's medical records, and an augmenter reality headset. The augmented reality headset technology and artificial intelligence are layered onto an improved manual system to minimize false positives and negatives, to improve the patient experience patient, resulting in cost savings for the doctor and patient and enabling portions of the allergy testing to be performed remotely from the office of the allergist, either by the patient or by a trained medical technician. The testing vials, the patient specific immunology vials, and the skin test target tags, will, in some embodiments, each deploy either radio frequency ID tags, Bluetooth low energy tags, or near field communication tags.

A second embodiment of the automated allergy office system of the present disclosure comprises back or arm target stickers used by artificial intelligence and augmented reality headset as sites such that the system determines target locations of where to perform scratch or injection points, wherein moles, skin tags, pre-existing rash, or tattoo, that may yield a false positive or negative display a message for a medical technician to move the back or arm target sticker to a scratch or injection point away from the mole, skin tags, pre-existing rash, or tattoo. If the patient has the mole, skin tags, pre-existing rash, or tattoo, as identified by the artificial intelligence or the augmented reality headset, a second test site is identified. The second test site reduces the likelihood of false positives and negatives. The automated allergy office system of the present disclosure may be initiated either in the office of the allergist or remotely. The automated allergy office system of the present disclosure may be periodically updated either in the office of the allergist or remotely.

A third embodiment of the automated allergy office system of the present disclosure including an augmented reality headset that projects target allergen injection points on the image of the back or arm of the patient relative to the target location wherein if the augmented reality headset detect a mole, skin tag, pre-existing rash, or tattoo, at the target location is moved to avoid the mole, skin tag, pre-existing rash, or tattoo. The augmented reality headset combined with voice recognition technology interprets spoken commands of a wearer of the augmented reality headset. The augmented reality headset reads and records the wheal color, wheal size and change in color as well as flare size. In another embodiment, the augmented reality headset also reads and records an infrared signature of a wheal reaction site and flare reaction site. A second embodiment of the automated allergy office system of the present disclosure also includes means for retesting negative test results. The retesting of the negative test results is performed using prefilled vials and syringes, wherein the augmented reality headset monitors the content of each vial, each vial location in a testing tray and the location of each skin tester. In addition, the augmented reality headset monitors injection sites and the location of the used skin testers and the location of used vials.

A fourth embodiment of the automated allergy office system of the present disclosure comprises artificial intelligence learning of the correct interpretation of wheal, flare, color, and infrared temperature measurement, including grading, the artificial intelligence through an augmented reality headset, recording each test site to ensure that a negative reaction does not occur to the injection. The augmented reality headset captures an image of a test site immediately after an allergen is administered. The augmented reality headset also captures an image of a test site at about a 15-minute interval after the tests are completed. The automated allergy office system of the present disclosure further comprise means for updating artificial intelligence models with current values. Such updated artificial intelligence models are designed for achieving optimal values while safeguarding patient identity in an artificial intelligence library.

Still other aspects of the processes for utilizing the automated allergy office of the present disclosure will become apparent to those skilled in this art from the following description wherein there is shown and described in the embodiments of this disclosure, simply by the way of illustration of the best modes contemplated for carrying out the present disclosure. As will be realized, the present disclosure is capable of different embodiments, and its several details are capable of modification in various, obvious aspects all without departing from the invention. Accordingly, the drawings and descriptions will be regarded as illustrative in nature and not as restrictive.

The database and artificial intelligence for reaction interpretation examines the size change of the wheal, the size change of the flare, any color change of the wheal and flare, and infrared measurement of any temperature change.

The artificial intelligence analysis is comprehensive. A printout of artificial intelligence analysis of wheals, flares, color, temperature, and grade. Paper, tablet, or computer accessible artificial intelligence analysis are provided for the doctor to evaluate and adjust as needed. Negative test results from the percutaneous scratch testing are retested with prefilled vials and syringes (the augmented reality headset read the content of each vial, their location in the testing trays as well as the location of each syringe, the augmented reality headset monitor the injection site as well as the location of the used syringes and the location of the used vials).

The verified negatives are recorded and merged with the initial percutaneous allergy test results. If a negative retest shows a positive from the intradermal injection retest, the data is merged with the initial test data for the doctor's analysis and conclusion.

After the doctor adjusts the artificial intelligence analysis, the data is entered into the patient's record and is used for the automatic preparation of the patient's immunological shot vials.

A copy of this record, with patient-specific data removed, is put into the artificial intelligence learning database, this will improve the artificial intelligence results in the future. A system of concentrated allergens, some being grouped together, are driven by the doctor's immunological plan with specific volumes pumped into the vials that will be used for the patient immunological shots. The system generates tags for each vial with the patient's name, contents, coded biometric data, expiration date, manufacturer, lot number of stock bottle, expiration date of stock bottle, stock source from manufacturer, vial temperature and the vial number (e.g. −1 of 4).

For examples of how artificial intelligence is used in the automated office of the present disclosure, see United States publication 20200202245 (Lesnik; et al.) entitled "A Probabilistic Data Classifier System and Method Thereof" filed Oct. 14, 2018, and United States publication 20190065464 (Finley; et al.) entitled "Artificial Intelligence Scribe" filed Mar. 8, 2018.

Before each shot is given to a patient, the unique patient identifier is checked to confirm patient identity, the patient's shot vials are scanned, and the injection volume is displayed for the nurse or medical technician. After the shot is given, the shot vials are scanned again. Finally, the artificial intelligence, through the augmented reality headset records each shot site to ensure that the patient does not experience a negative reaction to the injection. If the patient complains of a negative reaction, or if the augmented reality headset detects a negative reaction, an alert is given to the nurse, medical technician, and the doctor requesting immediate help. The time to administer the immunology shots is also recorded.

As the doctor, nurse, and medical personnel become familiar with the images and animation displayed in the augmented reality headset, he or she can choose to speed up or eliminate portions of the animation. However, the sped-up visuals will continue to display all the key elements of the display sequence to ensure that the proper process and procedure is followed.

As used herein, the term "augmented reality headset" refers to a relatively new technology that integrates information from the real world and the virtual world "seamlessly". Specifically, by means of techniques such as electronic computer processing, augmented reality technology applies virtual information to the real world by simulation and then superimposition, and the result is perceived by human senses. Therefore, a sensory experience that transcends reality is achieved. In this case, the real environment and the virtual object are superimposed in the same picture or space in real time. The augmented reality technology not only displays real-world information, but also displays virtual information at the same time, so that the two kinds of information complement and superimpose each other. In the visual augmented reality technology, the real world and computer graphics are multi-synthesized by using a helmet display. With maturity of the market, a variety of augmented reality products have emerged, especially head-mounted augmented reality headset. See, for example, United States publication 20200211420 (Buras; et al.) entitled "System and Method for Three-Dimensional Augmented Reality Guidance for Use of Medical Equipment" filed Dec. 26, 2019, and U.S. patent Ser. No. 10/197,803 (Badiali; et al.) entitled "Augmented Reality Glasses for Medical Applications and Corresponding Augmented Reality System" filed Mar. 27, 2015.

The automated allergy office of the present disclosure will result in portions of the allergy diagnosis and treatment moving out of the allergist's office to intermediate medical sites and to a certain degree of home testing, analysis, and treatment of allergies.

Still other aspects of the telehealth system of the present disclosure will become apparent to those skilled in this art from the following description wherein there is shown and described in the embodiments of this disclosure, simply by the way of illustration of the best modes contemplated for carrying out the present disclosure. As will be realized, the present disclosure is capable of different embodiments, and its several details are capable of modification in various, obvious aspects all without departing from the disclosure. Accordingly, the drawings and descriptions will be regarded as illustrative in nature and not as restrictive.

Throughout this application, various provisional applications, patents applications, PCT applications, and patents are referenced. The disclosures of these documents in their entireties are hereby incorporated by reference into this specification to more fully describe the state of the art to which this disclosure pertains.

As used herein, the phrase "at least one of A, B, and C" means all possible combinations of none or multiple instances of each of A, B, and C, but at least one A, or one B, or one C. For example, and without limitation: Ax1, Ax2+Bx1, Cx2, Ax1+Bx1+Cx1, Ax1+Bx12+Cx113. It does not mean Ax0+Bx0+Cx0.

The foregoing description of embodiments for this disclosure has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An automated allergy office system, comprising:
a target sticker for placement on a target location on a patient, wherein the target location is to be used for at least one of a scratch or injection point of an allergen from a vial delivered with a skin tester, and
an augmented reality headset for viewing the target location,
the augmented reality headset including artificial intelligence that visually identifies a skin discoloration, including at least one of moles, skin tags, rashes, and tattoos, and displays on the augmented reality headset a message for a medical technician to not place the target sticker on any detected skin discoloration.

2. The automated allergy office system of claim 1, wherein if the target location has the skin discoloration as identified by the artificial intelligence, a second target location is identified, wherein the second target location does not have aa skin discoloration.

3. The automated allergy office system of claim 1, wherein if the augmented reality headset detects skin discoloration at the target location, the target location is moved to avoid the skin discoloration on the patient.

4. The automated allergy office system of claim 1, wherein the augmented reality headset includes voice recognition technology that interprets spoken commands of a wearer of the augmented reality headset, and the augmented reality headset reads and records at least one of a wheal color and a wheal flare.

5. The automated allergy office system of claim 4, wherein the augmented reality headset reads and records an infrared signature of at least one of a wheal reaction site and flare reaction site.

6. The automated allergy office system of claim 1, wherein the augmented reality headset monitors at least one of a content of the vial and a location of the vial with the allergen that is used at the target location.

7. The automated allergy office system of claim 1, wherein the augmented reality headset monitors at least one of the target location, a location of the skin tester used at the target location, and a location of the vial used at the target location.

* * * * *